US007019094B2

(12) United States Patent
Westman et al.

(10) Patent No.: US 7,019,094 B2
(45) Date of Patent: Mar. 28, 2006

(54) INTERMEDIATE PRODUCTS, METHODS FOR THEIR PREPARATION AND USE THEREOF

(75) Inventors: Jacob Westman, Vänge (SE); Ronny Lundin, Ekerö (SE)

(73) Assignee: Biotage AB, Uppsala (SE)

(*) Notice: Subject to any disclaimer, the term of this patent is extended or adjusted under 35 U.S.C. 154(b) by 258 days.

(21) Appl. No.: 10/448,060

(22) Filed: May 30, 2003

(65) Prior Publication Data
US 2004/0005637 A1 Jan. 8, 2004

Related U.S. Application Data

(60) Provisional application No. 60/384,133, filed on May 31, 2002.

(51) Int. Cl.
C08F 116/36 (2006.01)
C08F 16/36 (2006.01)
C08F 216/36 (2006.01)

(52) U.S. Cl. ............... 526/316; 526/317.1; 526/227; 526/258; 526/347.2; 526/346

(58) Field of Classification Search ............... 526/316, 526/317.1, 227, 258, 347.2, 346
See application file for complete search history.

(56) References Cited

FOREIGN PATENT DOCUMENTS
WO 99/38993 A1 8/1999

OTHER PUBLICATIONS

Bhat, "A method for the rapid synthesis of benzopyrone libraries employing a resin capture strategy", J. Comb. Chem., 2, 597-599 (2000).*
Berteina et al., *SYNLETT*, Nov. 1998, pp. 1231-1233 (XP-001074013).
Stanovnik et al., *SYNLETT*, 2000, No. 8, pp. 1077-1091 (XP-002219156).
Larhed et al., *Drug Discovery Today*, Apr. 8, 2001, No. 6, pp. 406-416 (XP002901866).
Abdulla et al., *Tetrahedron*, 1979, vol. 35, pp. 1675-1735.

(Continued)

*Primary Examiner*—Ling-Sui Choi
(74) *Attorney, Agent, or Firm*—Birch, Stewart, Kolasch & Birch LLP

(57) ABSTRACT

Novel solid supported intermediate products of the general formula

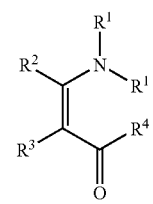

I coupled to a solid polymeric support through one or both of the $R^1$ groups or through the $R^4$ group which are suitable for synthesis of heterocyclic compounds are disclosed. Methods for preparing such intermediate products are also disclosed and also the use of the intermediate products in simple and fast methods on solid phase for synthesis of heterocycles.

11 Claims, 7 Drawing Sheets

OTHER PUBLICATIONS

Tietze, L., *Chem. Rev.*, 1996, vol. 96, pp. 115-136.
Gedye et al., *Tetrahedron Letters*, 1986, vol. 27, No. 3, pp. 279-282.
Wehler et al., *Tetrahedron Letters*, 1996, vol. 37, No. 27, pp. 4771-4774.

* cited by examiner

INTERMEDIATE PRODUCTS, METHODS FOR THEIR PREPARATION AND USE THEREOF

This application claims the benefit of Provisional Application No. 60/384,133, filed May 31, 2002.

FIELD OF THE INVENTION

The present invention relates to novel solid supported intermediate products suitable for synthesis of heterocyclic compounds and methods for preparing such intermediate products. The invention also relates to use of the intermediate products in simple and fast methods on solid phase for synthesis of heterocycles with large structural diversity in high yields and high purity.

BACKGROUND OF THE INVENTION

Highly functionalized heterocycles of various ring sizes, with different heteroatoms and substitution patterns are of major interest in the pharmaceutical and agricultural industry due to the many intrinsic biological properties of these substances.

In medicinal chemistry in general, and combinatorial chemistry in particular, the use of versatile synthons or versatile scaffolds, which are available after only a few reaction steps, are of great interest. An example of a reagent producing such synthons is N,N-dimethylformamide diethyl acetal (DMFDEA), cf. Abdulla, R. F.; Brinkmeyer, R. V., Tetrahedron, 1979, 35, 1675–1735. Condensation reactions between an activated methyl or methylene group adjacent to an ester or keto functionality and DMFDEA form dimethylaminopropenoates(A) or dimethylaminopropenones (B), see FIG. 1.

These intermediates, in which the dimethylamino moiety acts as a good leaving group, have been used in reactions in solution under conventional heating methods which has been described for example in Stanovnik, B.; Svete, J., Synlett, 2000, 8, 1077–1091. The intermediates could then be reacted with dinucleophiles to form different heterocycles. The availability of starting materials, which could form activated alkylaminopropenones or alkylaminopropenoates with DMFDEA is large and the number of possible heterocycles with large diversity, which are possible to form in a subsequential step from these types of intermediates is substantial. The formation of heterocycles from these intermediates takes place via a cascade or domino-type reaction, cf. Tietze, L. F., Chem. Rev., 1996, 115–136, which means that it involves two or more new bond formations taking place under the same reaction conditions. The advantages of this kind of reaction as compared to traditional multi-step reactions are simplified engineering, no intermediate work-up, minimized waste handling and lower cost of purification. All of these are important factors to consider when working the synthesis of combinatorial libraries.

Microwave heating has been used in organic synthesis since 1986, cf. Gedye, R.; Smith, F.; Westaway, K.; Ali, H.; Baldisera, L.; Laberge, L.; Rousell, J., Tetrahedron Lett. 1986, 27, 279–282. Microwave heating reduces the reaction times in comparison with traditional heating. In addition, the yields of the reactions are often increased and the time for optimizing the reaction conditions is minimized in comparison to conventional heating methods.

SUMMARY OF THE INVENTION

The present invention relates in one aspect to new intermediate products of the general formula I suitable for synthesis of heterocyclic compounds.

In another aspect the present invention relates to methods for preparing intermediates of formula I.

According to another aspect the invention relates to the use of an intermediate product of the general formula I for synthesis of heterocyclic compounds.

BRIEF DESCRIPTION OF THE DRAWINGS

FIG. 7 shows examples of synthesis of heterocycles via solid phase bound dialkylamino propenones.

DETAILED DESCRIPTION OF THE INVENTION

More closely the invention relates to an intermediate product suitable for synthesis of heterocyclic compounds which intermediate compound has the general formula I

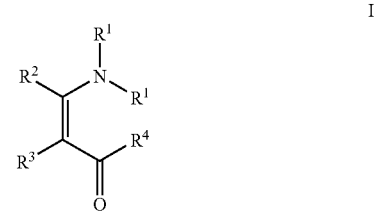

coupled to a solid polymeric support through one or both of the $R^1$ group(s) or through the $R^4$ group wherein when coupled to the polymeric support through $R^1$ The $R^1$ groups represent the same or different groups chosen from lower alkyl with 1 to 6 carbon atoms, such as methyl, ethyl, cycloalkyl with 3 to 6 carbon atoms in the ring, such as cyclopentyl, cyclohexyl, heterocyclic compounds including one or more heteroatoms, benzyl groups. Two $R^1$ groups together can be included in a heterocyclic ring containing one or more nitrogen atoms;

$R^2$ represents H or a lower alkyl with 1 to 6 carbon atoms, such as methyl;

R⁴ represents unsubstituted or substituted aromatic ring(s), unsubstituted or substituted heteroaromatic ring(s) with one or more heteroatoms, or OR⁵; when R⁴ is unsubstituted or substituted aromatic ring(s), unsubstituted or substituted heteroaromatic ring(s), R³ represents H, alkyl, unsubstituted or substituted aromatic ring, unsubstituted or substituted heteroaromatic ring with one or more heteroatoms, or COOR⁵;

when R⁴ is OR⁵, R³ is CN, COOR⁵, NCOR⁵, NCOOR⁵, or COR⁵;

the R⁵ groups, which can be the same or different, represent H, alkyl, benzyl, unsubstituted or substituted aromatic ring(s), unsubstituted or substituted heteroaromatic ring(s) with one or more heteroatoms;

and wherein when coupled to the polymeric support through R⁴

R¹ and R² are as defined above,
R³ is as defined above except COOR⁵ and COR⁵,
R⁴=OR⁵ where R⁵ is as defined above except H.

When producing a large number of substances in solution the subsequent purifications will be time-consuming. However, it has according to the present invention been found that solid phase technique, which allows for easy automation together with microwave assisted heating, gives rise to unexpected advantages such as high yields of the heterocyclic compounds with high purity and possibility to eliminate time-consuming purification steps, which are necessary when producing heterocyclic compounds in solution according to the above mentioned prior art. Furthermore, in the method according to the present invention a large excess of reagent could be used in a reaction with a resin bound substrate whereby the reaction is driven to completion. The redundant amount of reagent could then be removed by a simple filtration. Furthermore, by the use of microwave heating in solid phase synthesis in accordance with the present invention the reaction times in the heterogeneous systems can be substantially shortened as compared to other methods of heating.

Figure 1:
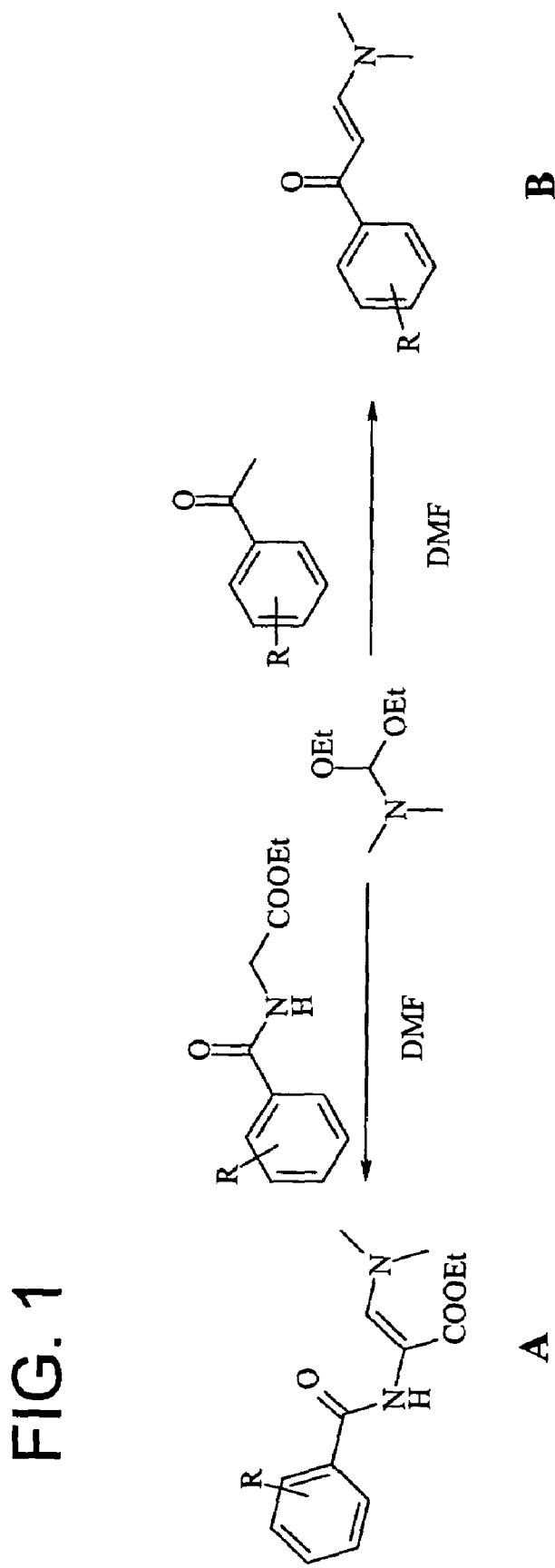
FIG. 1 shows condensation reactions between an activated methyl or methylene group adjacent to an ester or keto functionality and DMFDEA form dimethylaminopropenoates(A) or dimethylaminopropenones (B)
Figure 2:
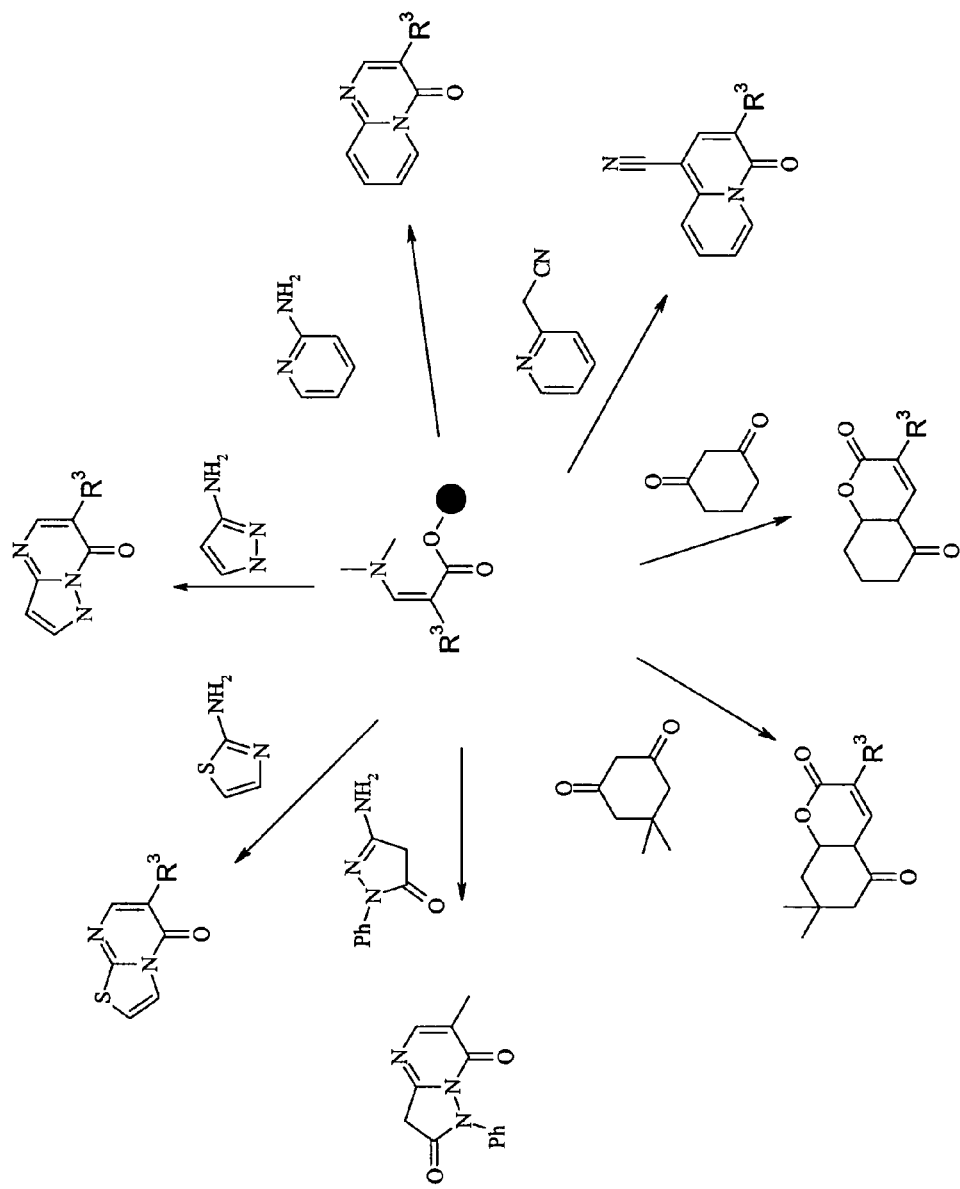
FIG. 2 shows examples of heterocyclic compounds prepared by reaction of intermediate products according to the present invention, 3-dimethylamino propenoates, with different dinucleophiles are illustrated.

The intermediate products according to the present invention are suitable to use for preparing heterocyclic compounds by reaction with dinucleophiles and in FIG. 2 examples of heterocyclic compounds prepared by reaction of intermediate products according to the present invention, 3-dimethylamino propenoates, with different dinucleophiles are illustrated.

Figure 3:
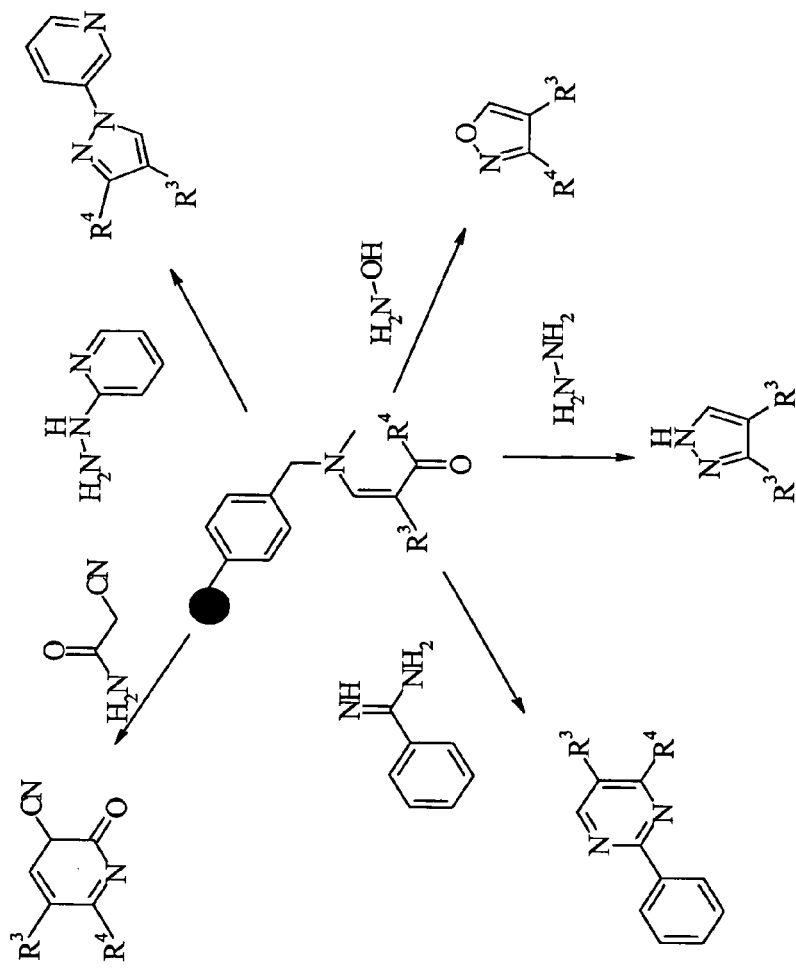
FIG. 3 shows examples of heterocyclic compounds prepared by reaction of intermediate products according to the present invention, 3-dimethylamino propenones, with different dinucleophiles are illustrated.

In FIG. 3 examples of heterocyclic compounds prepared by reaction of intermediate products according to the present invention, 3-dimethylamino propenones, with different dinucleophiles are illustrated.

The solid polymeric support to which the compounds are coupled could be the following: a.) beads, pellets, disks, fibers, gels, or particles such as cellulose beads, pre-glass beads, silica gels, polypropylene beads, polyacrylamide beads, polystyrene beads that are lightly cross-linked with 1–2% divinylbenzene and optionally grafted with polyethylene glycol and optionally functionalized with amino, hydroxy, carboxy or halo groups; and b.) soluble supports such as low molecular weight non-cross-linked polystyrene and polyethylene glycol. The term solid support is used interchangeably with the term resin or bead in this invention and is intended to mean the same thing. For propenoates any resin which can form an alkyl or benzylic ester from a carboxylic acid such as polystyrene-divinylbenzene resins eg. Merrifield resin (benzyl chloride handle), Wang resin (benzyl alcohol handle), Tentagel PHB (benzyl alcohol handle), Resin with PAM anchor, Rink resin, PEGA resin are examples of suitable resins. For propenones any resin with a dialkyl amine handle, any resin which can form a dialkyl amine or benzyl alkyl amine handle such as Merrifield resin (displacement of a chloride with an alkylamine), Rink resin (methylation of a primary amine with methyliodide), amino methyl resin, trisamine resin, SASRIN resin, Behring resin, PAM resin, N-methylaminomethyl resin HCl are examples of suitable resins for use as solid support.

In the methods for preparing the intermediates according to the present invention N-disubstituted carboxamide acetals of the general formula II are suitable to use as a reactant

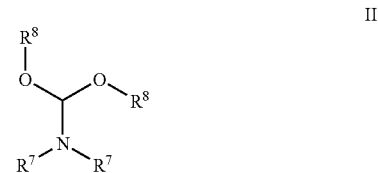

II wherein the two R⁷ groups are the same or different groups selected from alkyl groups with 1 to 6 carbon atoms, cycloalkyl groups with 3 to 6 carbon atoms, benzyl groups, cyclic compounds including heterocyclic compounds with one or more heteroatoms, R⁷ is suitably methyl, ethyl. The two R⁷ groups could together be part of a carbocyclic or heterocyclic ring, for example imidazole.

The two R⁸ groups are the same or different groups selected from straight, branched or cyclic alkyl chains, substituted such alkyl chains, benzyl groups. R⁸ is suitably Me, Et. The two R⁸ groups could together be part of a carbocyclic ring for example 1,3 dioxane.

In a method of preparing an intermediate of formula I, which is coupled to the solid polymeric support through one or both R¹ groups (propenones) a polymeric support with a reactive secondary amine is prepared according to the following reaction whereby a product of formula IV is obtained

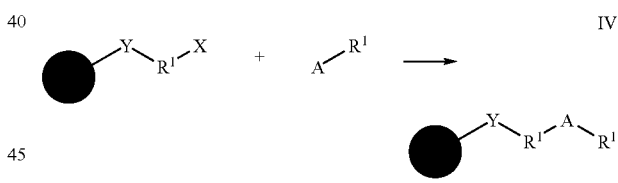

IV wherein Y is a spacer group which can be alkyl, benzyl, trityl or [OCH₂CH₂]ₙ, R¹ is as defined in claim 1, X is NH₂, halogen or triflate. When X is NH₂, A is halogen or triflate, and when X is halogen or triflate, A is NH₂, which product of formula IV then is reacted with a N-substituted carboxamide acetal of the general formula II as defined above and a substance with a methylene or methyl group adjacent to a keto function according to the general formula III

III where R³, R⁴ are as defined in claim 1, whereby a compound of formula I coupled to the polymeric support through one or both of the R¹ groups is obtained.

In another method of preparing an intermediate of formula I, which is coupled to the solid polymeric support through one or both of the $R^1$ groups (propenones), a polymeric support with a reactive secondary amine is prepared according to the following reaction, whereby a product of formula V is obtained

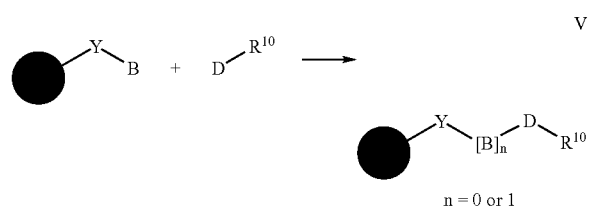

wherein Y is as defined above, $R^{10}$ is a secondary amine, B and D are functional groups which form a covalent bond when reacted with each other, and when n=0, B is a leaving group, which product of formula V then is reacted with a N-disubstituted carboxamide acetal of the general formula II as defined above
and a substance with a methylene or methyl group adjacent to a keto function according to the general formula III as defined above, whereby a compound of formula I coupled to the polymeric support through one or both of the $R^1$ groups is obtained.

In a method of preparing an intermediate of formula I, which is coupled to the solid polymeric support through the $R^4$ group (propenoates) a polymeric support of the general formula VI

with a reactive X end group, wherein X and Y are as defined in claim 2, is reacted with a compound of the general formula VII

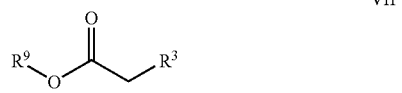

wherein $R^3$ is defined as in claim 1 and $R^9$ is H, alkyl, benzyl or phenyl, whereby a product of the formula VIII

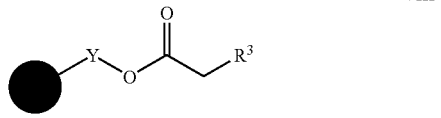

is obtained, which product of formula VIII then is reacted with a N-disubstituted carboxamide acetal of the general formula II as defined above, whereby a compound of formula I is obtained which is coupled to the solid polymeric support through the $R^4$ group.

In the above methods for preparing the intermediates according to the present invention it is suitable to carry out the reactions by means of heating. The heating is suitably induced by the use of microwaves. The temperature is generally between 100 and 250° C. It is often suitable to carry out the reactions in a closed vessel.

The intermediate products according to the present invention are useful for the synthesis of heterocyclic compounds wherein a solid supported intermediate compound of the general formula I is reacted with a dinucleophile, i.e. a substance with two nucleophilic atoms selected from N, C, O and S adjacent to each other or separated by one or more carbon atoms, by heating the intermediate compound and the dinucleophilic substance in a solution for a short period of time which, after evaporation of the solvent, produces the desired heterocyclic compound in high yield and high purity.

The heating is suitably induced by the use of microwaves and a useful temperature is between 100 and 250° C. The reaction time needed is short and suitably less than 30 minutes.

Dialkylamino propenoates coupled to a solid support react with dinucleophiles in a two-step reaction wherein substitution of the dialkylamino group is followed by a nucleophilic attack on the ester functionality, which cleaves the ester.

Dialkylamino propenones coupled to a solid support react in a somewhat different manner with dinucleophiles. A condensation reaction with the keto function is followed by the substitution of the dialkylamino group.

Heterocycle formation from dialkylamino propenones and dialkylamino propenoates. The intermediates could be reacted with many dinucleophiles such as hydrazines, amidines, diketo substrates and 2-amino-pyridines to form heterocyclic compounds such as isoxazoles, pyrazoles, chromones, pyrimidines, pyranones, pyrimidones, pyranones, pyrimidones and substituted 4H-quinolizin-4-ones all of which have great interest as potential druglike compounds. Many of the mentioned products have in the literature been described to induce biological activity.

Dinucleophiles are defined as any substances with two nucleophilic atoms adjacent to each other or separated by one or more carbon atoms. The nucleophilic atoms are chosen from N, C, O, S. Examples of suitable dinucleophiles are hydroxylamine, hydrazine, substituted hydrazines, substituted amidines, 2-aminopyridines, 2-pyridino acetonitrile, 2-aminopyrazoline, 2-aminopyridazine, substituted 1,3-diketohexane and cyclohexane, 2-aminothiazole and 3-amino-2-pyraxolin-5-ones. Examples of some dinucleophiles are illustrated below.

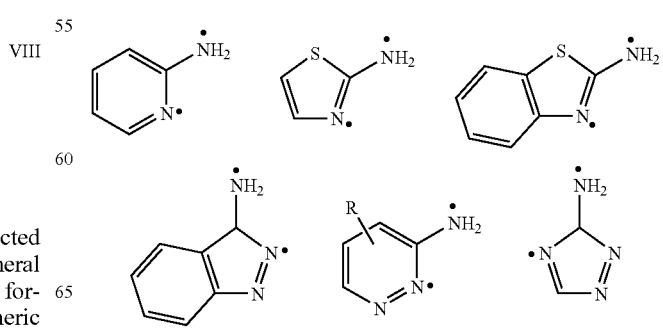

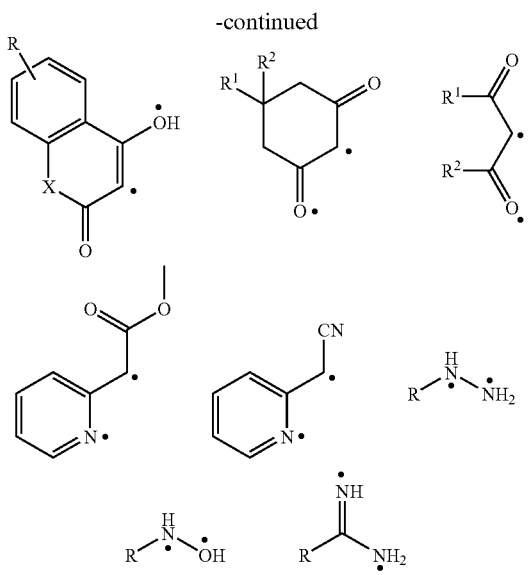

The dots indicate the nucleophilic atoms

Synthesis of Solid Phase Bound Dialkylamino Propenoates

Figure 4:
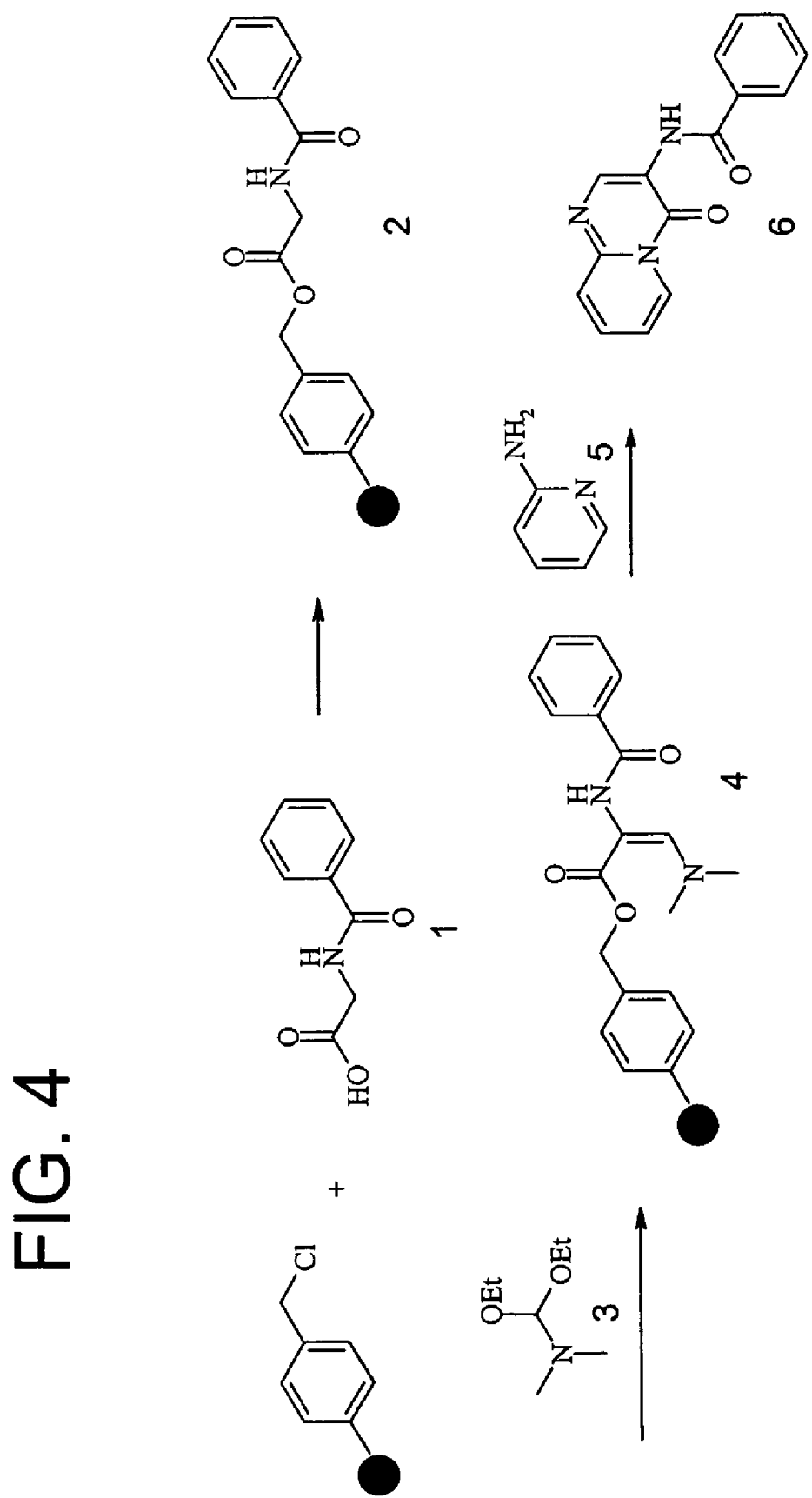
FIG. 4 shows an example of the formation of an intermediate product wherein the substrate is bound to the solid resin could be carried out in a two-step reaction.

Formation of an intermediate product wherein the substrate is bound to the solid resin could be carried out in a two-step reaction, an example of which is shown in FIG. 4.

FIG. 4 shows the reaction between a solid support, Merrifield resin, and hippuric acid (1) in the first step and reaction of the product formed (2) with DMFDEA (3) which gives the intermediate product (4). Magic angle spinning NMR (MAS-NMR) analysis (Wehler, T.; Westman, J. *Tetrahedron Lett*. 1996, 37, 4771–4774) was used for the protocol development. An ester linkage was formed between the carboxylic acid substrate and the solid phase resin in step one. By comparing the peak area from the methylene group in the resin handle (PhCH$_2$Cl) and the peak area from the solid phase benzylester methylene group (PhCH$_2$OCO) the yield could be determined. In this example the Merrifield resin was treated with the N-acylated glycine derivative (hippuric acid) together with cesium carbonate in DMF under microwave heating at 200° C. for 10 minutes. MAS-NMR analysis and elemental analysis showed a loading of approximately 1 mmol/g (80% yield), which is in the same range as described in the literature but in approximately a 100-fold shorter reaction time. Merrifield resin was suitable to use due to the high loading capacity and high thermal stability. After washing the resin was mixed with 5 eq. DMFDEA in 2.5 ml DMF and exposed to microwaves at 180° C. for 10 minutes to form the dimethylamino propenoate intermediate product 4 according to the invention.

Synthesis of Solid Phase Bound Dialkylamino Propenones

Figure 5:
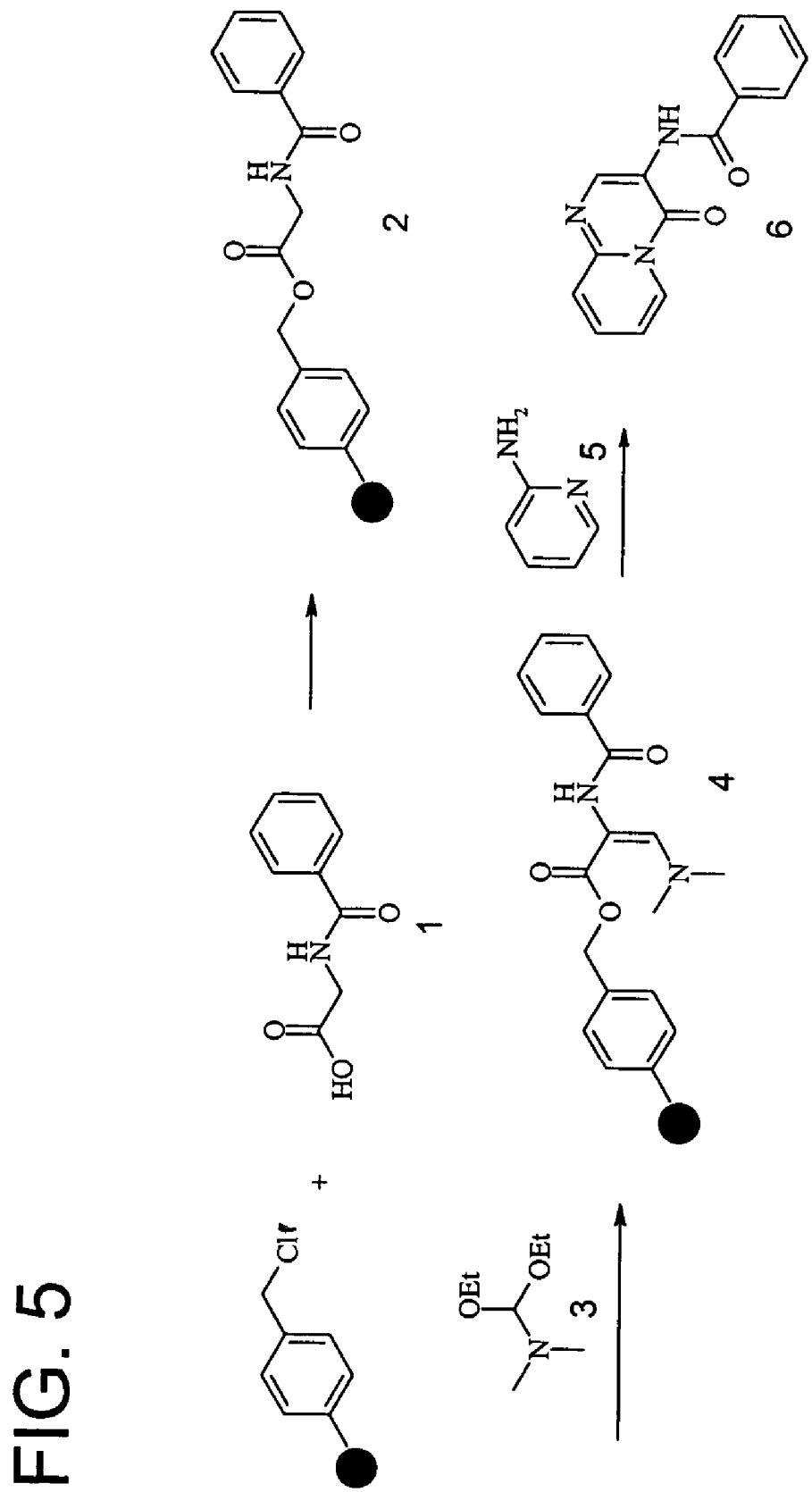
FIG. 5 shows an example of a synthesis method for preparing solid phase bound dialkylamino propenones.

An example of a synthesis method for preparing solid phase bound dialkylamino propenones is illustrated in FIG. 5.

In the first step in this synthesis Merrifield resin was treated with methyl amine in water under microwave heating at 150° C. for 10 minutes to form a benzyl methyl amine on the solid resin (13). After washing the resin was treated with 5 eq. DMFDEA together with 5 eq. 4-phenoxyacetophenone under microwave heating at 180° C. for 10 minutes in DMF to form the intermediate product [14], the solid supported benzyl methyl aminopropenone according to the present invention in a three-component reaction.

The intermediate products according to the present invention were then used for the synthesis of heterocycles by reacting the solid supported intermediates with dinucleophiles in a suitable solvent e.g. at 180° C. for 10 min.

Figure 6:
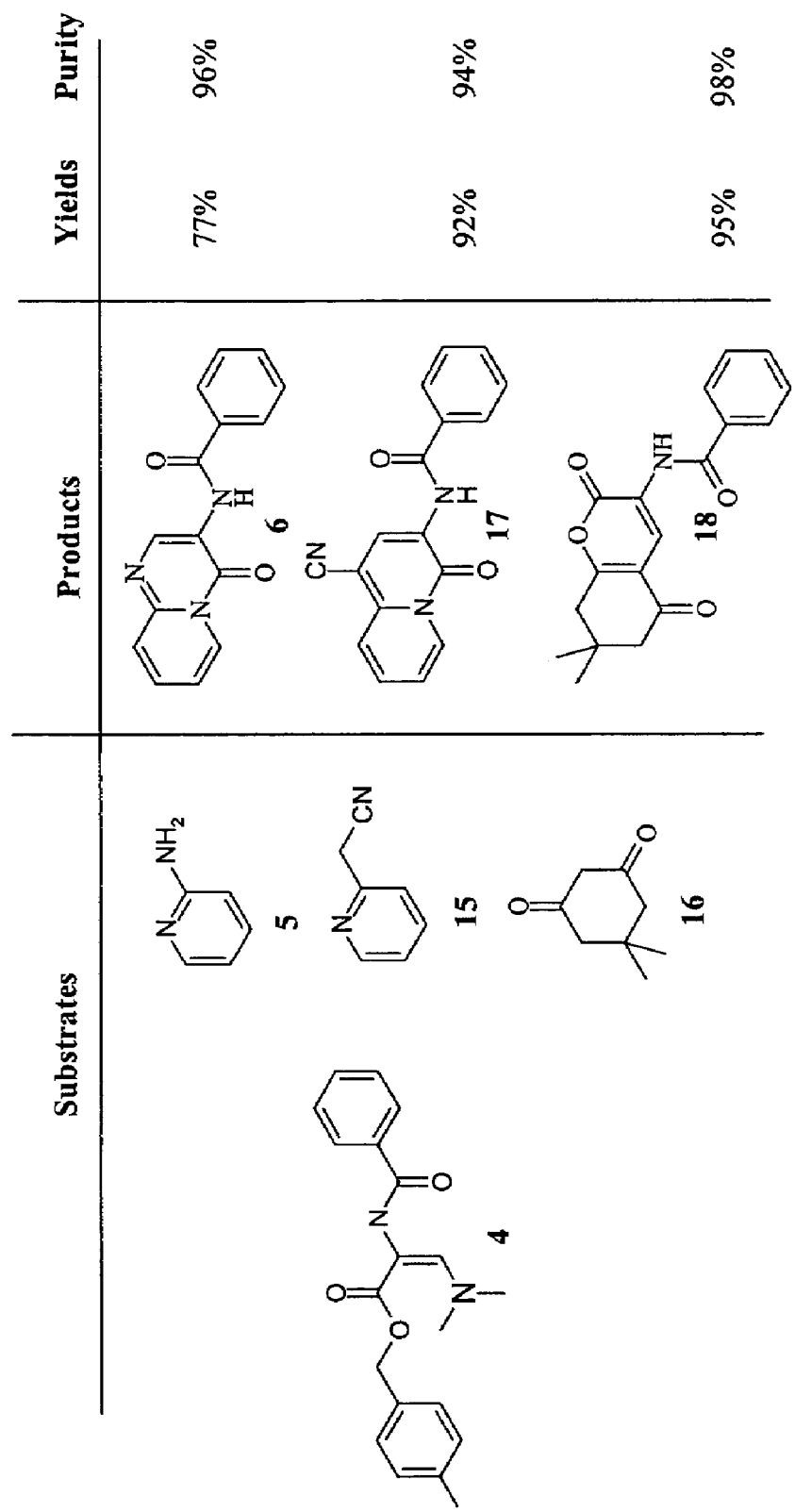
FIG. 6 shows examples of synthesis of heterocycles via solid phase bound dialkylamino propenoates.

In FIG. 6 examples of synthesis of heterocycles via solid phase bound dialkylamino propenoates are illustrated.

Figure 7:
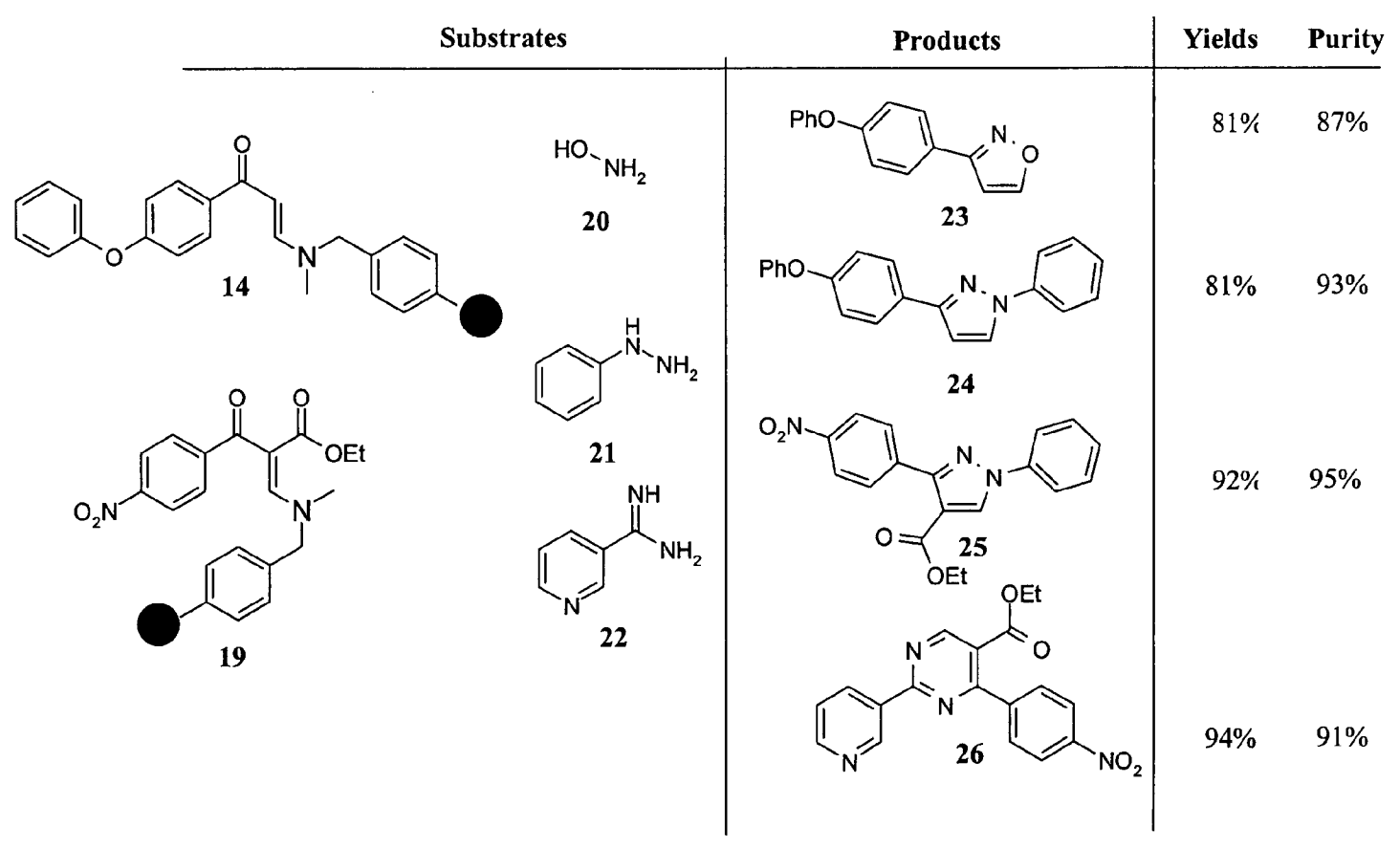

In FIG. 7 examples of synthesis of heterocycles via solid phase bound dialkylamino propenones are illustrated.

The invention is illustrated by means of the following examples, which are presented only for illustrative purpose and are not meant to limit the scope of the invention in any way.

EXAMPLES

The microwave-assisted reactions were performed in a single mode microwave cavity, an instrument from Personal Chemistry. NMR spectra were recorded in CDCl$_3$ or DMSO-d$_6$ at 25° C., using a Bruker at 300 MHz ($^1$H)/75 MHz ($^{13}$C) or a Varian 600 MHz instrument with a Nano probe for the MAS-NMR analysis. All NMR spectra recorded were in agreement with the postulated structures and only selected data are reported. Elemental analyses were performed by Mikrokemi AB, Uppsala, Sweden. All starting reagents were of the best grade available (Aldrich or Lancaster) and were used without purification. The reactions were run in a closed vessel and that in several cases the pressure during the reaction was between 5–20 bar.

Coupling of N-benzoyl glycine to Merrifield resin (2). 200 mg Merrifield resin (1.25 mmol/g loading capacity) was swelled in 2.5 mL DMF, 1.25 mmol (5 equiv.) N-benzoyl glycine (Hippuric acid) (1) and 1.25 mmol Cs$_2$CO$_3$ were added and the reaction mixture was heated at 200° C. for 10 min. The reaction mixture was then cooled down to room temperature by pressurized air. The residue was then washed several times with DMF, water and DCM. The resin was dried under reduced pressure in a desiccator. MAS-NMR analysis indicated compound 2 in a yield of 80% (approx. 1.0 mmol/g loading). 1H NMR (CDCl3): δ 4.24 (COCH$_2$NCO), 5.11 (PhCH$_2$CO), 7.3–7.4 (4H, aromatic), 7.8 (1H, aromatic). Elemental analysis: 1.35 weight percent giving 0.96 mmol/g loading.

Methylamination f Merrifield resin (13). 200 mg Merrifield resin (1.25 mmol/g loading capacity) was treated with 2.0 mL methylamine in water (40% w/w) (excess) at 150° C. for 5 min. The reaction mixture was then cooled to room temperature by pressurized air. The residue was washed several times with Water, DCM and MeOH to give compound 13. Elemental analysis gave 1.52 weight percent giving approx. 1.08 mmol/g loading.

Dimethyl amino propenoates from N-benzoyl glycine on solid support (4). 250 mg of solid supported N-benzoyl glycine benzyl ester 2 (approximately 0.25 mmol) was swelled in 2.5 mL DMF, 1.57 mmol DMFDEA was added and the reaction mixture was heated at 180° C. for 10 min. The reaction mixture was then cooled to room temperature by pressurized air. The residue was washed several times with DMF, water and DCM. The resin was dried under reduced pressure in a desiccator. MAS-NMR analysis indicate compound 4 but no yield was determined due to low resolution.

Benzyl methyl amino propenones from 4-phenoxy acetophenone on solid support (14). 200 mg of benzyl methylamine on solid support 13 (approximately 0.2 mmol) was swelled in 2.0 mL DMF, 214 µL DMFDEA and 155 µL 4-phenoxy acetophenone were added and the reaction mixture was heated at 180° C. for 10 min. The reaction mixture was then cooled down to room temperature by pressurized air. The residue was washed several times with DMF, water and DCM. The resin was dried under reduced pressure in a desiccator. MAS-NMR analysis indicated compound 14 but no yield was determined due to low resolution.

Benzyl methyl amino propenones from ethyl 4-nitrobenzoylacetate on solid support (19). 200 mg of Benzyl methylamine on solid support 13 was treated with ethyl 4-nitrobenzoylacetate as described above for the synthesis of compound 19. MAS-NMR analysis indicated compound 19 but no yield was determined due to low resolution.

3-(benzoyl)amino-4H-pyrido[1,2-a]pyrimidin-4-ne (6.) 100 mg of the solid supported compound 4 were added to 6.6 mg 2-aminopyridine (5) (0.07 mmol) in 0.5 mL of acetic acid. The solution was exposed to microwaves at 180° C. for 10 minutes and then cooled to room temperature. The acetic acid was evaporated giving 14.2 mg of product 6, a total yield of 77% and 96% purity based on LC/MS analysis. The structure was confirmed by $^1$H NMR (300 MHz, CDCl$_3$): δ 7.16 (dt, 1H, ArH), 7.45–7.65 (m, 4H, ArH), 7,75 (dd, 1H, ArH), 7.95 (dd, 2H, ArH), 8.84 (s, 1H, NH), 8.95 (dd, 1H, ArH), 9.75 (s, 1H, pyrimidin-H).

3-(benzoyl)amino-1-cyano-4H-quinolizin-4-one (17). 100 mg of the solid supported compound 4 were added to 5.6 μL 2-pyridyl-acetonitrile (15) (0.05 mmol) in 0.5 mL of acetic acid. The solution was exposed to microwaves at 180° C. for 10 minutes and then cooled to room temperature. The acetic acid was evaporated. The residue was dissolved in DCM and filtered through a plug of silica. Crude analysis showed a LC/MS purity of 94%. Evaporation of the solvent gave the product 17 in 13.3 mg, a total yield of 92%. The structure was confirmed by $^1$H NMR (300 MHz, CDCl$_3$): δ NMR 7.02 (ddd, 1H, ArH), 7.32–7.42 (m, 4H, PhH), 7.77 (m, 2H, ArH), 7.81 (dt, 1H, ArH), 8.88 (s, 1H, NH), 8.92 (dt, 1H, ArH), 9.11 (s, 1H, quinolizin-4-one).

3-(benzoyl)amino-5-oxo-5,6,7,8-tetrahydro-2H-1-benzopyran-2-one (18). 100 mg of the solid supported compound 4 were added to 7.0 mg 5,5 dimethyl-1,3-cyclohexanedione (16) in 0.5 mL of acetic acid. The solution was exposed to microwaves at 180° C. for 10 min. and then cooled to room temperature. The acetic acid was evaporated giving 14.8 mg of product 18, a total yield of 95% and 98% purity based on LC/MS analysis. The structure was confirmed by $^1$H NMR (300 MHz, CDCl$_3$): δ 1.2 (s, 6H, CH$_3$) 2.48 (s, 2H, CH$_2$), 2.78 (s, 2H, CH$_2$), 7.5–7.7 (m, 3H, ArH), 7.92 (m, 2H, ArH), 8.59 (s, 1H, NH), 8.83 (s, 1H, CH).

(4-phenoxy)phenylisoxazole (23). 200 mg of the solid supported compound 14 was mixed with 0.1 (0.5 equiv.) mmol of hydroxylamine hydrochloride (20) and 2 mL of EtOH. The mixture was exposed to microwaves at 180° C. for 10 minutes and then cooled to room temperature. The solvent was evaporated. The product 23 was isolated in 81% yield and 87% purity based on LC/MS analysis and characterized by $^1$H NMR (300 MHz, CDCl$_3$): δ 6.44 (d, 1H, J=1.9 Hz, isoxazole), 7.04 (m, 4H, ArH), 7.17 (dt, 1H, ArH), 7.38 (m, 2H, ArH), 7.76 (m, 2H, ArH), 8.25 (d, 1H, J=1.9 Hz, isoxazole).

1-phenyl-5-(4-phenoxyphenyl)-pyrazole (24). 200 mg of the solid supported compound 14 was mixed with 0.1 (0.5 equiv.) mmol of phenylhydrazine (21) and 2 mL of acetic acid. The mixture was exposed to microwaves at 180° C. for 10 minutes and then cooled to room temperature. The solvent was evaporated. The product 24 was isolated in 81% yield and 93% purity and characterized by $^1$H NMR (300 MHz, CDCl$_3$): δ 6.48 (d, 1H, J=1.9 Hz, pyrazole), 6.91 (dd, 2H, ArH), 7.03 (m, 2H, ArH), 7.18 (dd, 2H, ArH), 7.3–7.4 (m, 8H, ArH), 7.71 (d, 1H, J=1.9 Hz, pyrazole).

Ethyl (1-phenyl-3-(4-nitro)-phenyl pyrazole-4-carboxylate (25). 200 mg of the solid supported compound 19 were treated as described for compound 24 using EtOH as solvent. The EtOH was evaporated giving 31.0 mg of product 25 in 92% yield and 91% purity. The structure was confirmed by $^1$H NMR (300 MHz, CDCl$_3$): δ 1.28 (t, 3H, CH$_3$CH$_2$), 4.25 (q, 2H, CH$_2$CH$_3$), 7.20 (m, 2H, ArH), 7.35 (m, 3H, ArH), 7.51 (d, 2H, ArH), 8.21 (d, 2H, ArH), 8.23 (s, 1H, pyrazole).

Ethyl 2-(4-pyridyl)-4-(4-nitrophenyl)-pyrimidine-5-carboxylate (26). 200 mg of the solid supported compound 19 in 2 mL DMF was treated with 0.1 mmol (approx. 0.5 equiv.) 4-amidinopyridine hydrochloride (22) and 0.15 mmol KOH, exposed to microwaves at 180° C. for 10 minutes and then cooled to room temperature. The solvent was evaporated. The product (26) was isolated in 94% (32.7 mg) in 91% purity. The structure was characterized by $^1$H NMR (300 MHz, CDCl$_3$): δ 1.22 (t, 3H, CH$_3$CH$_2$), 4.28 (q, 2H, CH$_2$CH$_3$), 7.54 (m, 3H, PhH), 7.85 (m, 2H, PhH), 8.35 (dd, 2H, pyridyl), 8.56 (dd, 2H, pyridyl), 9.31 (s, 1H, pyrimidine).

According to the present invention activated aminopropenoates and aminopropenones on solid phase are provided which intermediate products can be used in combinatorial syntheses of a large number of different heterocycles with an overall reaction time of approximately 30 minutes to give the products in high purity in high to excellent yields. One major benefit obtained by this approach is that purification is not needed.

What is claimed is:
1. An intermediate product suitable for synthesis of heterocyclic compounds which is a compound of the general formula I

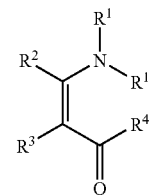

coupled to a solid polymeric support through the $R^4$ group
  $R^1$ groups represent the same or different groups chosen from lower alkyl with 1 to 6 carbon atoms, cycloalkyl with 3 to 6 carbon atoms in the ring, heterocyclic compounds including one or more heteroatoms, benzyl groups; two $R^1$ groups together can be included in heterocyclic ring containing one or more nitrogen atoms;
  $R^2$ represents H or a lower alkyl with 1 to 6 carbon atoms;
  $R^4$ represents unsubstituted or substituted aromatic ring(s), unsubstituted or substituted heteroaromatic ring(s), with one or more heteroatoms, or $OR^5$;
  when $R^4$ is unsubstituted or substituted aromatic ring(s), unsubstituted or substituted heteroaromatic ring(s), $R^3$ represents H, alkyl, unsubstituted or substituted aromatic ring, unsubstituted or substituted heteroaromatic ring with one or more heteroatoms,
  when $R^4$ is $OR^5$, $R^3$ is CN, NCOR$^5$, or NCOOR$^5$; the $R^5$ groups, which can be the same or different, represent alkyl, benzyl, unsubstituted or substituted aromatic ring(s), unsubstituted or substituted heteroaromatic ring(s) with one or more heteroatoms.

2. The intermediate product according to claim 1, wherein with $R^1$ lower alkyl is methyl or ethyl and cycloalkyl is cyclopentyl or cyclohexyl and with $R^2$ lower alkyl is methyl.

3. A method of preparing an intermediate of formula I according to claim 1 which is coupled to the solid polymeric support through the $R^4$ group (propenoates), wherein a polymeric support of the general formula VI

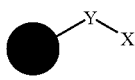

VI with a reactive X end group, wherein Y is a spacer group which can be alkyl, benzyl, trityl or $[OCH_2CH_2]_n$, and X is $NH_2$, halogen or triflate, is reacted with a compound of the general formula VII

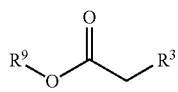

VII wherein $R^3$ is as defined in claim 1 and $R^9$ is H, alkyl, benzyl or phenyl, whereby a product of the formula VIII

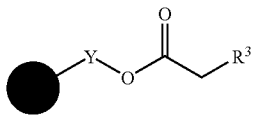

VIII is obtained, which product of formula VIII then is reacted with a N-disubstituted carboxamide acetal of the general formula II

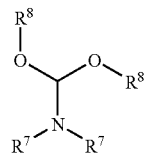

II wherein the $R^7$ groups are different or the same chosen from C1–C6 alkyl, cycloalkyl with 3 to 6 carbon atoms, benzyl groups, cyclic compounds including heteroatoms, the two $R^7$ groups could together be part of a carbocyclic or heterocyclic ring, the $R^8$ groups could be the same or different chosen from straight, branched or cyclic alkyl chains, benzyl groups, and alkyl chains with substituents; the two $R^8$ groups could together be part of a carbocyclic ring;

whereby a compound of formula I is obtained which is coupled to the solid polymeric support through the $R^4$ group.

4. A method according to claim 3 wherein the reactions are performed under heating.

5. A method according to claim 4, wherein the heating is induced by the use of microwaves.

6. A method according to claim 3 where the solid polymeric support to which the compounds are coupled is polystyrene beads that are lightly crosslinked with 1–2% divinylbenzene and optionally grafted with polyethylene glycol.

7. A method according to claim 6 where the solid polymeric support is polystyrene beads which are functionalized with halogen and triflate or $NH_2$.

8. A method according to claim 6 where the polystyrene beads are functionalized.

9. A method according to claim 3 where the polystyrene beads are functionalized with halogen or hydroxyl.

10. A method according to claim 3 wherein the disubstituted carboxamide acetal of formula II is dimethylformamide diacetal.

11. A method for the synthesis of heterocyclic compounds which comprises reacting the intermediate product of claim 1 and a dinucleophile for a short period of time in a solvent; and evaporating the solvent to produce the desired heterocyclic compound in high yield and in high purity.

* * * * *